(12) United States Patent
Lee et al.

(10) Patent No.: US 9,510,076 B2
(45) Date of Patent: Nov. 29, 2016

(54) WATERPROOF EARPHONE STRUCTURE

(71) Applicant: Kingstate Electronics Corporation, New Taipei (JP)

(72) Inventors: Ting-Wei Lee, New Taipei (TW); Chia-Yuan Tang, New Taipei (TW); Cheng-Yang Lo, New Taipei (TW)

(73) Assignee: Kingstate Electronics Corporation, New Taipei (TW)

( * ) Notice: Subject to any disclaimer, the term of this patent is extended or adjusted under 35 U.S.C. 154(b) by 0 days.

(21) Appl. No.: 14/950,107

(22) Filed: Nov. 24, 2015

(65) Prior Publication Data

US 2016/0269823 A1 Sep. 15, 2016

(30) Foreign Application Priority Data

Mar. 12, 2015 (TW) .............................. 104203657 U
Sep. 17, 2015 (TW) .............................. 104215077 U (51) Int. Cl.
| | |
|---|---|
| *H04R 1/44* | (2006.01) |
| *H04R 1/10* | (2006.01) |
| *H04R 25/00* | (2006.01) |
| *A61F 11/08* | (2006.01) |

(52) U.S. Cl.
CPC ............. *H04R 1/1016* (2013.01); *A61F 11/08* (2013.01); *H04R 1/1066* (2013.01); *H04R 1/44* (2013.01); *H04R 25/652* (2013.01)

(58) Field of Classification Search
CPC .... H04R 1/44; H04R 1/1016; H04R 1/1066; H04R 1/10; H04R 1/105; H04R 1/1075; H04R 5/033

USPC ........................... 381/334, 332, 87, 370, 182
See application file for complete search history.

(56) References Cited

U.S. PATENT DOCUMENTS

| | | | | |
|---|---|---|---|---|
| 8,670,586 | B1* | 3/2014 | Boyle | H04R 1/1008 381/189 |
| 2012/0195455 | A1* | 8/2012 | Chiba | H04R 1/1091 381/374 |
| 2012/0219167 | A1* | 8/2012 | Yoong | H04R 25/654 381/325 |
| 2014/0064548 | A1* | 3/2014 | Chu | H04R 1/1091 381/380 |
| 2015/0289051 | A1* | 10/2015 | Tung | H04R 1/44 381/334 |

* cited by examiner

*Primary Examiner* — Ahmad F Matar
*Assistant Examiner* — Sabrina Diaz
(74) *Attorney, Agent, or Firm* — Juan Carlos A. Marquez; Marquez IP Law Office, PLLC (57) ABSTRACT

Disclosed is a waterproof earphone structure including a main body with a rear cavity and a front cavity for installing a waterproof module and a shielding module respectively, and a speaker body installed in the main body. The waterproof module includes first and second waterproof elements installed in the rear and front cavities of the main body respectively. This structure not just allows users to sense external sounds only, but also improves low-frequency noise interference and water-resistance. Since the first and second waterproof elements are formed with pores having a diameter smaller than 0.6 mm and arranged apart from one another, external low-frequency noises are suppressed. Further, the effect of surface tension prevents water from entering into waterproof devices or soaking the interior of the earphone. Users enjoy good sound quality since the sound is transmitted through the pores. In addition, the shielding module provides an anti-dust effect.

18 Claims, 11 Drawing Sheets

WATERPROOF EARPHONE STRUCTURE

BACKGROUND OF THE INVENTION

1. Technical Field

The present invention relates to an earphone structure, and more particularly, to a waterproof earphone structure capable of resisting water, avoiding sound distortion, and balancing the pressure, temperature and humidity inside/outside an auditory canal.

2. Description of Related Art

All liquids (wherein water is also a liquid) have surface tension which is formed by the cohesion of liquid molecules. In a liquid, each molecule is attracted or repelled by adjacent molecules in all directions, so that the resultant force of the molecular forces exerted on the molecules inside the liquid is substantially zero.

However, the attraction and repulsion exerted on the liquid molecules at a liquid-gas interface in all directions are unbalanced, so that the molecules at the surface layer of the liquid are attracted towards the inside of the liquid, and some of the molecules at the surface layer are pulled towards the inside of the liquid, and the surface area of the liquid is reduced, and such phenomenon is called surface tension.

Figure 10:
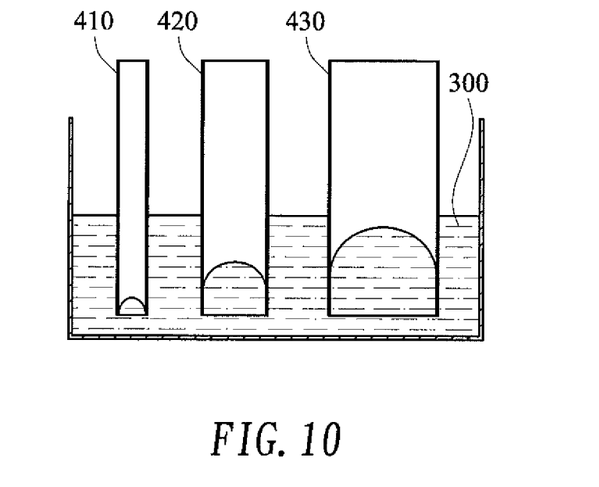
FIG. 10 is a schematic view showing the relation between tube diameter and surface tension of water.

With reference to FIG. 10 for the relationship between surface tension and tube diameter, the smaller the tube diameter, the greater the surface tension. Ends of a first tube 410, a second tube 420, and a third tube 430 arranged in an ascending orders of tube diameters are sequentially filled with a liquid 300. As the tube diameter increases, the surface tension decreases, so that a greater quantity of liquid 300 enters into the tube.

In general, an earplug of earphones or hearing aids generally does not have a waterproof function, and the conventional earphones or hearing aids may be damaged easily when they are soaked or splashed with liquid or water. Even worse, the liquid or water may enter into a user's ear and cause discomfort or injury to the user's ear.

In view of the aforementioned problem, it is an important subject for designers and developers of the related industry to design and develop an earphone structure capable of resisting water by the principle of surface tension, and such earphone structure not just resists water or liquid only, but also maintains original sound quality, balances the pressure, humidity and temperature inside/outside an auditory canal, and provides a comfortable and ergonomic earphone or earplug.

SUMMARY OF THE INVENTION

The present invention relates a waterproof earphone structure, comprising: a main body; a speaker body; and a waterproof module, wherein the waterproof module includes a plurality of pores formed therein. With the implementation of the present invention, the waterproof earphone structure not just complies with the ergonomic requirements and reduces noises entered from the outside only, but also achieves the effects of resisting water by the plurality of pores, balancing the pressure, temperature and humidity inside/outside the auditory canal, and preventing sound distortion.

The present invention provides a waterproof earphone structure comprising a main body, a speaker body and a waterproof module, wherein the main body includes a rear cavity, a cavity module and a front cavity, wherein the rear cavity is a hollow block with an end surface being formed as an opening and the other end being penetrated to form a penetrating hole, and a receptacle is protruded and formed on an inner wall of the rear cavity, configured to be corresponsive to the penetrating hole, and communicated to the penetrating hole, and the receptacle has a diameter smaller than the diameter of the penetrating hole, and a waterproof bushing is installed to a peripheral wall of the rear cavity, communicated to the interior of the rear cavity, and tightly fitted with the rear cavity; the front cavity is a hollow block installed at the opening of the rear cavity; and the cavity module is a circular body sheathed on an end of the front cavity and installed between the rear cavity and the front cavity; the speaker body is installed in the main body and has an audible end installed in the front cavity and configured to be corresponsive to a hollow position of the front cavity; the waterproof module is installed in the rear cavity of the main body and has a first waterproof element, and the first waterproof element has a block with a plurality of pores, and the pores are arranged, penetrated, and formed at the first waterproof element, and the pores at two opposite end surfaces of the first waterproof element are in form of apertures, and the first waterproof element is installed at the receptacle of the rear cavity and abutted at an inner wall of the receptacle, and the first waterproof element has an end surface disposed in the rear cavity and the other end surface facing outward.

Implementation of the present invention at least involves the following inventive steps:

1. Incurring a low manufacturing cost, reducing noises entered from the outside, and complying with ergonomic requirements.
2. Resisting water.
3. Balancing the pressure, temperature and humidity inside/outside an auditory canal.
4. Preventing sound distortion, and maintaining original sound quality.

The features and advantages of the present invention are detailed hereinafter with reference to the preferred embodiments. The detailed description is intended to enable a person skilled in the art to gain insight into the technical contents disclosed herein and implement the present invention accordingly. In particular, a person skilled in the art can easily understand the objects and advantages of the present invention by referring to the disclosure of the specification, the claims, and the accompanying drawings.

BRIEF DESCRIPTION OF THE SEVERAL VIEWS OF THE DRAWINGS

The invention as well as a preferred mode of use, further objectives and advantages thereof will be best understood by reference to the following detailed description of illustrative embodiments when read in conjunction with the accompanying drawings, wherein.

DETAILED DESCRIPTION OF THE EMBODIMENTS OF THE INVENTION

Figure 1:
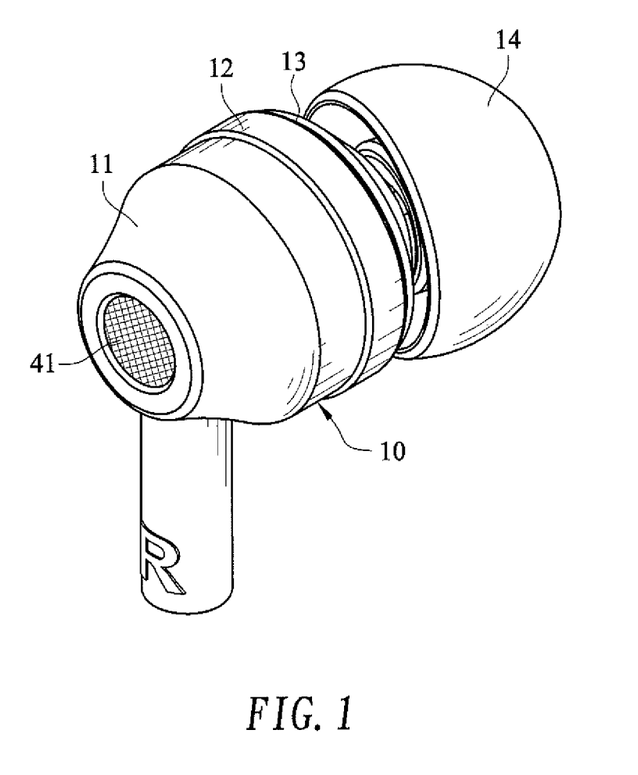
FIG. 1 is a perspective view of a waterproof earphone structure in accordance with a preferred embodiment of the present invention.
Figure 2:
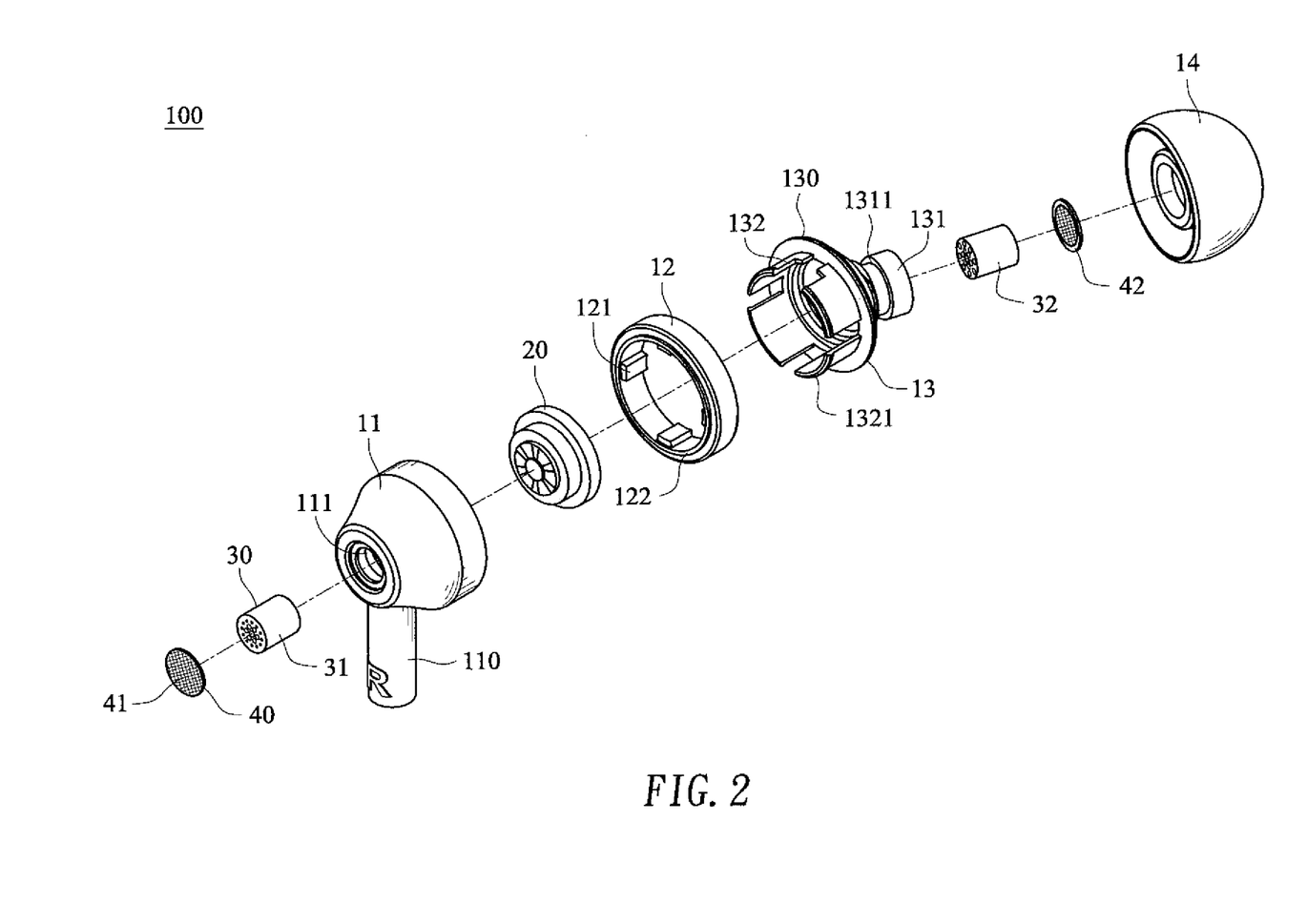
FIG. 2 is an exploded view of a waterproof earphone structure in accordance with a preferred embodiment of the present invention.

With reference to FIGS. 1 and 2 for a waterproof earphone structure 100 in accordance with a preferred embodiment of the present invention, the waterproof earphone structure 100 comprises a main body 10, a speaker body 20, a waterproof module 30, and a shielding module 40.

Figure 3:
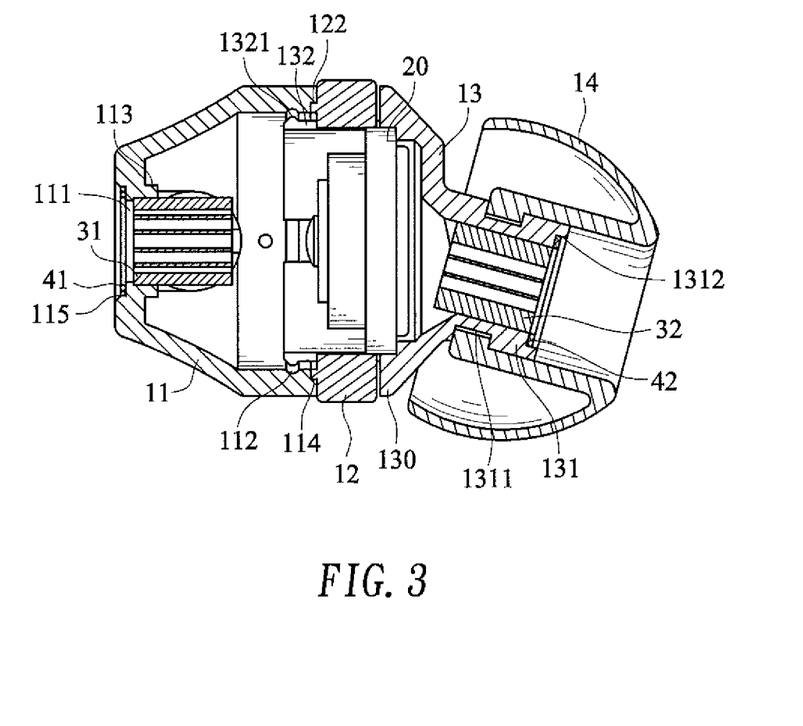
FIG. 3 is a cross-sectional view of a waterproof earphone structure in accordance with a preferred embodiment of the present invention.
Figure 4A:
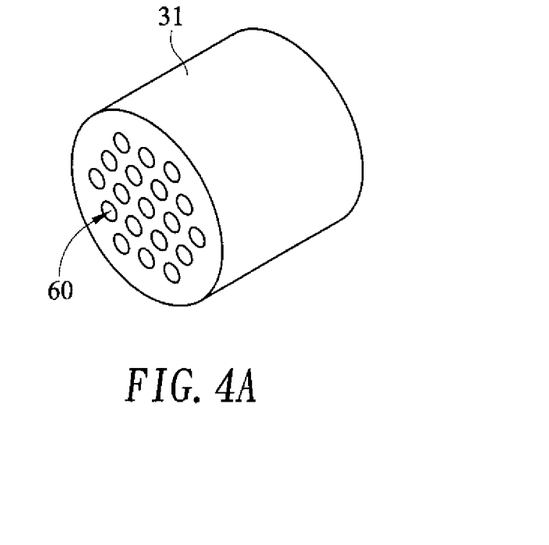
FIG. 4A is a perspective view of a first waterproof element and a pore in accordance with a preferred embodiment of the present invention.
Figure 4B:
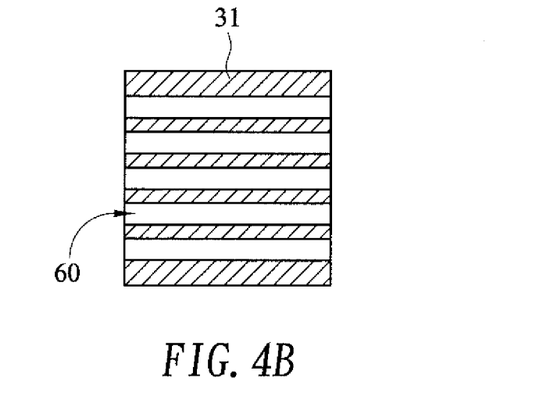
FIG. 4B is a cross-sectional view of a first waterproof element and a pore in accordance with a preferred embodiment of the present invention.
Figure 4C:
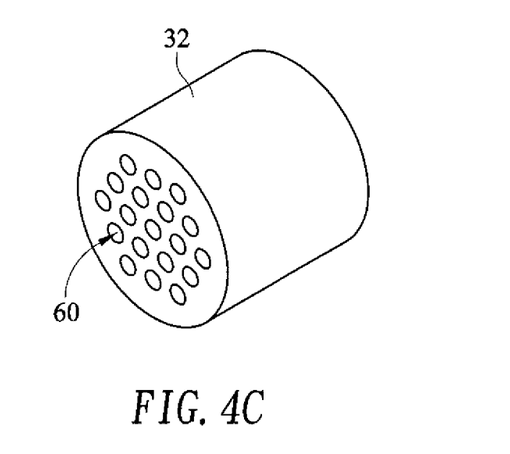
FIG. 4C is a perspective view of a second waterproof element and a pore in accordance with a preferred embodiment of the present invention.
Figure 4D:
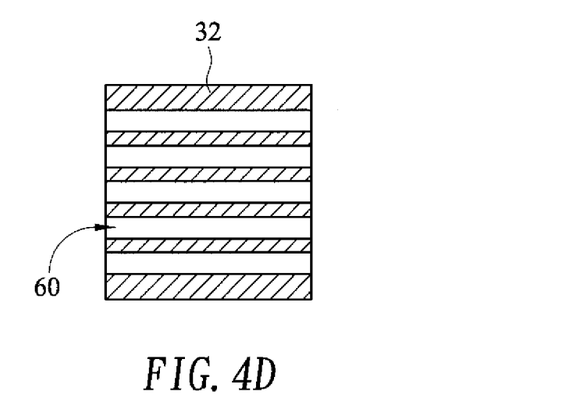
FIG. 4D is a cross-sectional view of a second waterproof element and a pore in accordance with a preferred embodiment of the present invention.

In FIGS. 2 and 3, the main body 10 includes a rear cavity 11, a cavity module 12, and a front cavity 13.

The rear cavity 11 is a hollow block having an end surface formed as an opening, and the other end surface being penetrated to form a penetrating hole 111, and a receptacle 113 is protruded and formed on an inner wall of the rear cavity 11, configured to be corresponsive to the penetrating hole 111, and communicated to the penetrating hole 111, and the receptacle 113 has a diameter smaller than the diameter of the penetrating hole 111, and a first mounting slot 115 is depressed and formed at the end surface of the rear cavity 11 forming the penetrating hole 111, and communicated to the penetrating hole 111, and a groove 112 is depressed and formed on an inner wall of the opening of the rear cavity 11, and a circular base 114 is depressed and formed at the end surface of the opening of the rear cavity 11; and a waterproof bushing 110 is installed to a peripheral wall of the rear cavity 11, communicated to the interior of the rear cavity 11, and tightly fitted with the rear cavity 11 to provide a waterproof function.

The front cavity 13 is a hollow block installed at the opening of the rear cavity 11 and includes a mounting portion 130, an output tube 131 and an extension portion 132, and the mounting portion 130 and the output tube 131 are formed at two opposite ends of the front cavity 13 respectively, and the output tube 131 is protruded and formed at the front cavity 13, and the mounting portion 130 is depressed and formed at the center position of the front cavity 13, and a circular slot 1311 is depressed and formed on an outer wall of the output tube 131, and a through hole is axially formed on the output tube 131 and communicated to the mounting portion 130, and a second mounting slot 1312 is depressed and formed at an end surface of the output tube 131 and communicated to the through hole, and the extension portion 132 is axially protruded and formed at the end surface of the front cavity 13 forming the mounting portion 130; specifically, the extension portion 132 has a plurality of plates arranged apart with each other and formed at the mounting portion 130, and the extension portion 132 has a flange 1321 radially protruded and formed on an outer wall of the extension portion 132 and opposite to the other end of the mounting portion 130, and an end of the extension portion 132 forming the flange 1321 is accommodated in the opening of the rear cavity 11, and the flange 1321 of the extension portion 132 is latched into the groove 112 of the rear cavity 11.

The cavity module 12 is a circular body sheathed on an end of the front cavity 13 and installed between the rear cavity 11 and the front cavity 13, and the cavity module 12 has a plurality of protrusions 121 arranged apart from each other and protruded from an inner wall of the cavity module 12, and a circular engaging portion 122 is protruded and formed at an end of the cavity module 12; the extension portion 132 of the front cavity 13 is passed through a gap formed by the protrusions 121, and the engaging portion 122 of the cavity module 12 is installed at the circular base 114 of the rear cavity 11.

The main body 10 further includes an earmuff 14, and the earmuff 14 is a hollow cover covered onto the circular slot 1311 of the output tube 131 of the front cavity 13, and a hollow position of the earmuff 14 is configured to be corresponsive to the through hole of the output tube 131.

The speaker body 20 is installed at the mounting portion 130 of the front cavity 13, and an audible end of the speaker body 20 is configured to be corresponsive to the hollow positions of the front cavity 13, the output tube 131 and the earmuff 14, and an audio signal line of the speaker body 20 is penetrated through the waterproof bushing 110 for transmitting signals with the outside; and the speaker body 20 is a prior art and thus will not be described in details.

The waterproof module 30 is installed in the rear cavity 11 and the front cavity 13 of the main body 10, and the waterproof module 30 includes a first waterproof element 31 and a second waterproof element 32, and the first waterproof element 31 and the second waterproof element 32 have a block with a plurality of pores 60, and the pore has a diameter smaller than 0.6 mm, and the pores 60 are arranged apart with one another and penetrated and formed at the first waterproof element 31 and the second waterproof element 32, and the pores 60 at two opposite ends of the first waterproof element 31 and the second waterproof element 32 are apertures; the first waterproof element 31 is installed at a receptacle 113 of the rear cavity 11 and abutted at the inner wall of the receptacle 113, and the first waterproof element 31 has an end surface disposed in the rear cavity 11 and the other end surface facing outward, and the second waterproof element 32 is installed in the through hole of the output tube 131 and coupled to the inner wall of the output tube 131, and the second waterproof element 32 has an end surface configured to be corresponsive to the audible end of the speaker body 20 and the other end surface installed at a hollow position in the earmuff 14.

The shielding module 40 is installed at the rear cavity 11 and the front cavity 13 of the main body 10 and has a first shielding element 41 and a second shielding element 42; the first shielding element 41 is installed at the first mounting slot 115 of the rear cavity 11 and covered onto an end of the first waterproof element 31 facing outward, and the second shielding element 42 is installed in the second mounting slot 1312 of the output tube 131 of the front cavity 13 and covered onto the second waterproof element 32; specifically, the first shielding element 41 and the second shielding element 42 have a breathable mesh cloth.

By installing the waterproof module 30 to the rear cavity 11 and the front cavity 13 of the main body 10, the present invention not just allows users to sense external sounds only, but also provides a waterproof effect. Since the first waterproof element 31 and the second waterproof element 32 of the waterproof module 30 are structures formed by a plurality of pores with a diameter smaller than 0.6 mm and arranging apart from one another, so that external low-frequency noises are suppressed by the pore structure of the waterproof device. In addition, when water flows to the end surfaces of the first waterproof element 31 and the second waterproof element 32, the water cannot pass through the pores of the first waterproof element 31 and the second waterproof element 32 due to surface tension, so as to prevent water from entering into the earphone.

When an external sound source enters into the rear cavity 11 through the pores 60 of the first waterproof element 31 and users hear the content of the sound while sensing the external sound, the structure of the pores 60 of the first waterproof element 31 not just suppresses low-frequency noises only, but also provides a good air permeability for the second waterproof element 32 to improve the hot and stuffy condition of the earphone over a long time of use, and the sound source produced by the speaker body 20 is transmitted through the pores 60 of the second waterproof element 32, so that user receives sounds with good sound quality and tone and without distortion.

In addition, the first shielding element 41 and the second shielding element 42 of the shielding module 40 installed at the rear cavity 11 and front cavity 13 provide an anti-dust effect.

In FIGS. 4A to 4D, each of the pores 60 formed in the first waterproof element 31 or the second waterproof element 32 is penetrated through the first waterproof element 31 or the second waterproof element 32, and each pore 60 is designed with a diameter to prevent water molecules to pass through the pore 60 due to surface tension.

Figure 5A:
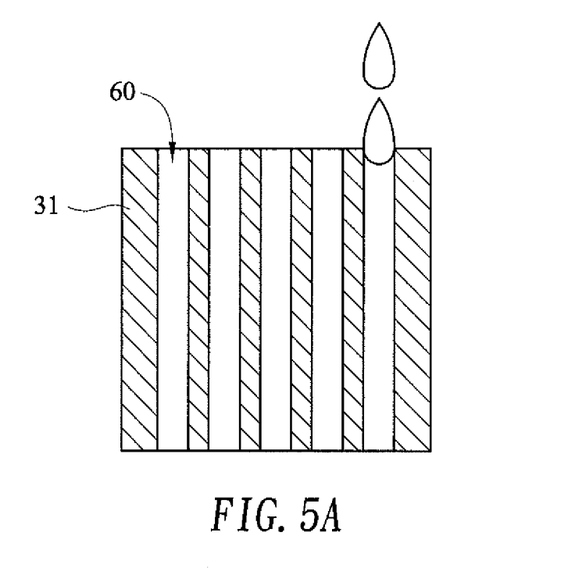
FIG. 5A is a schematic view showing the water resistance of a first waterproof element in accordance with a preferred embodiment of the present invention.
Figure 5B:
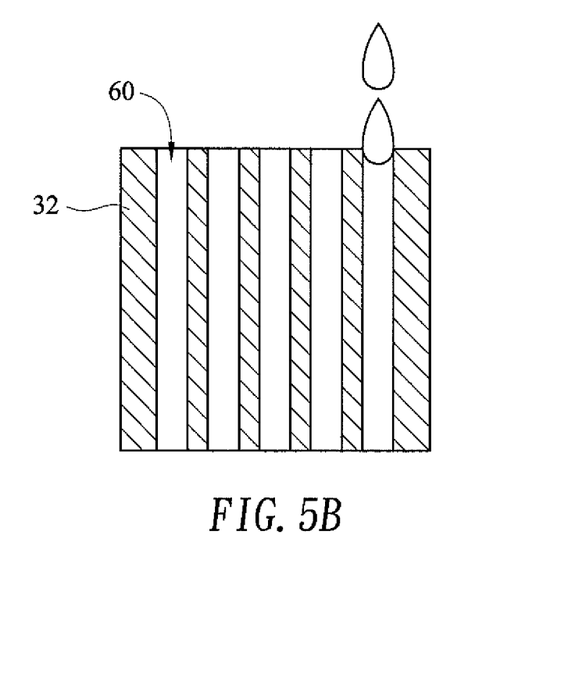
FIG. 5B is a schematic view showing the water resistance of a second waterproof element in accordance with a preferred embodiment of the present invention.
Figure 6:
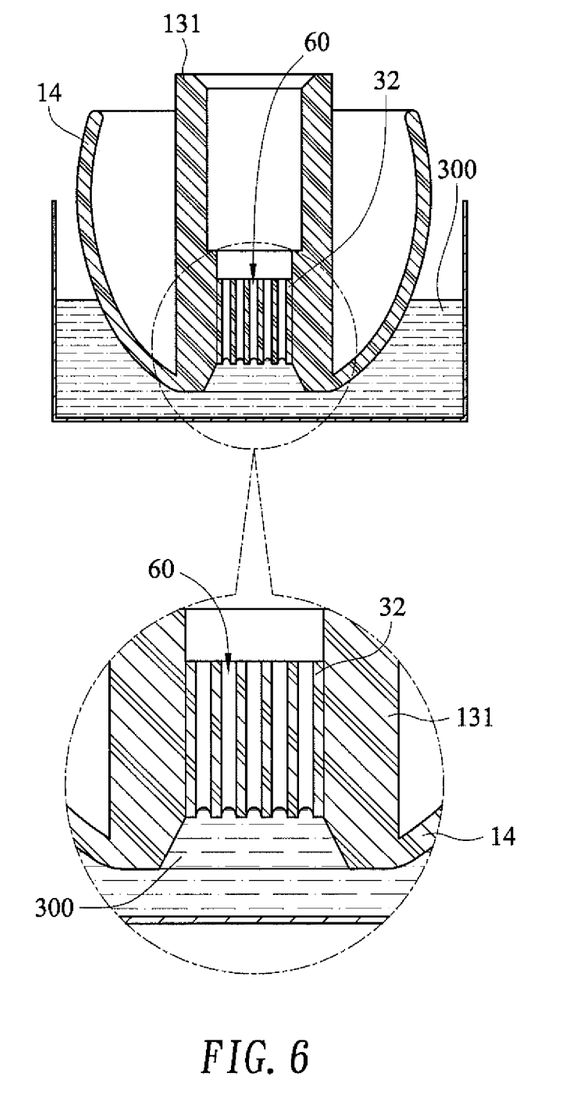
FIG. 6 is a schematic view showing the water resistance of a waterproof earphone structure in accordance with a preferred embodiment of the present invention.
Figure 7A:
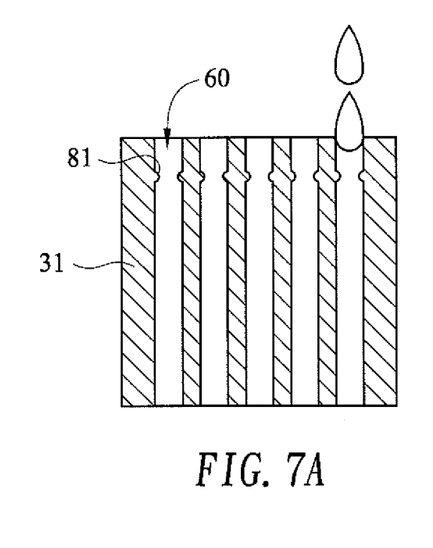
FIG. 7A is a schematic view showing the water resistance a pore of a first waterproof element having a bump in accordance with a preferred embodiment of the present invention.
Figure 7B:
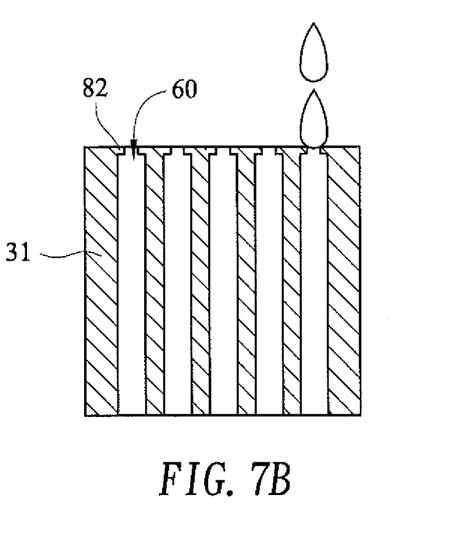
FIG. 7B is a schematic view showing the water resistance of a pore of a first waterproof element having a convex edge in accordance with a preferred embodiment of the present invention.
Figure 7C:
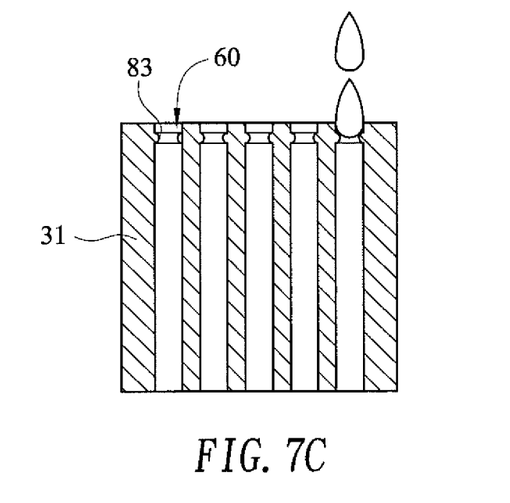
FIG. 7C is a schematic view showing the water resistance of a pore of a first waterproof element having a rim in accordance with a preferred embodiment of the present invention.
Figure 8A:
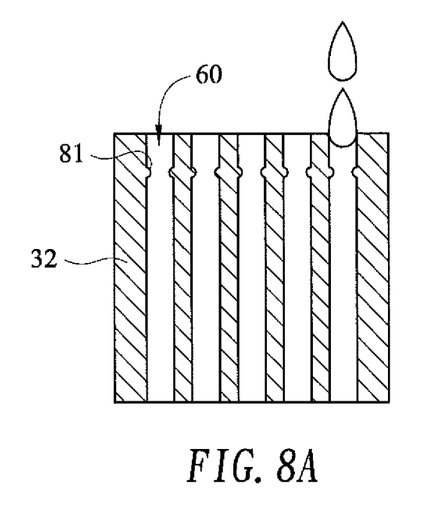
FIG. 8A is a schematic view showing the water resistance of a pore of a second waterproof element having a bump in accordance with a preferred embodiment of the present invention.
Figure 8B:
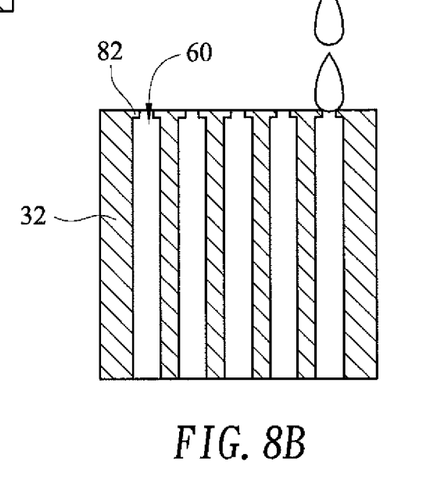
FIG. 8B is a schematic view showing the water resistance of a pore of a second waterproof element having a convex edge in accordance with a preferred embodiment of the present invention.
Figure 8C:
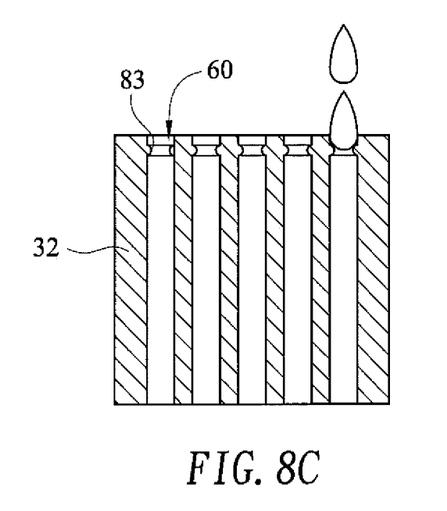
FIG. 8C is a schematic view showing the water resistance of a pore of a second waterproof element having a rim in accordance with a preferred embodiment of the present invention.

In FIGS. 5A and 5B, the pore 60 is designed with a diameter from 0.1 mm to 0.6 mm and a length from 1 mm to 5 mm to achieve an obvious and effective surface tension effect for preventing water molecules to pass through the pore 60.

On the other hand, the pores 60 of the first waterproof element 31 or the second waterproof element 32 may be arranged into the shape of a matrix, a circle, a square, a triangle, an oval, or even arranged into an irregular shape, without any specific limitation.

In FIGS. 4A to 5B and 6, the pores 60 with appropriately selected diameter and length can prevent the liquid 300 to pass through the pores 60 due to surface tension, so that the waterproof earphone structure 100 has the waterproof effect to prevent the liquid 300 from entering into the earphone structure, and the waterproof capacity is up to the IPX7 waterproofing standard. In other words, the waterproof earphone structure 100 may be put into water with the depth of one meter for the time up to 30 minutes without losing the waterproof effect.

In FIGS. 7A to 8C, at least one bump 81, at least one convex edge 82 or at least one rim 83 is formed on the surface of the pores 60 to improve the water resistance of the pores 60 formed in the first waterproof element 31 or the second waterproof element 32 for prevent water or liquid to pass through the pores 60.

Figure 9:
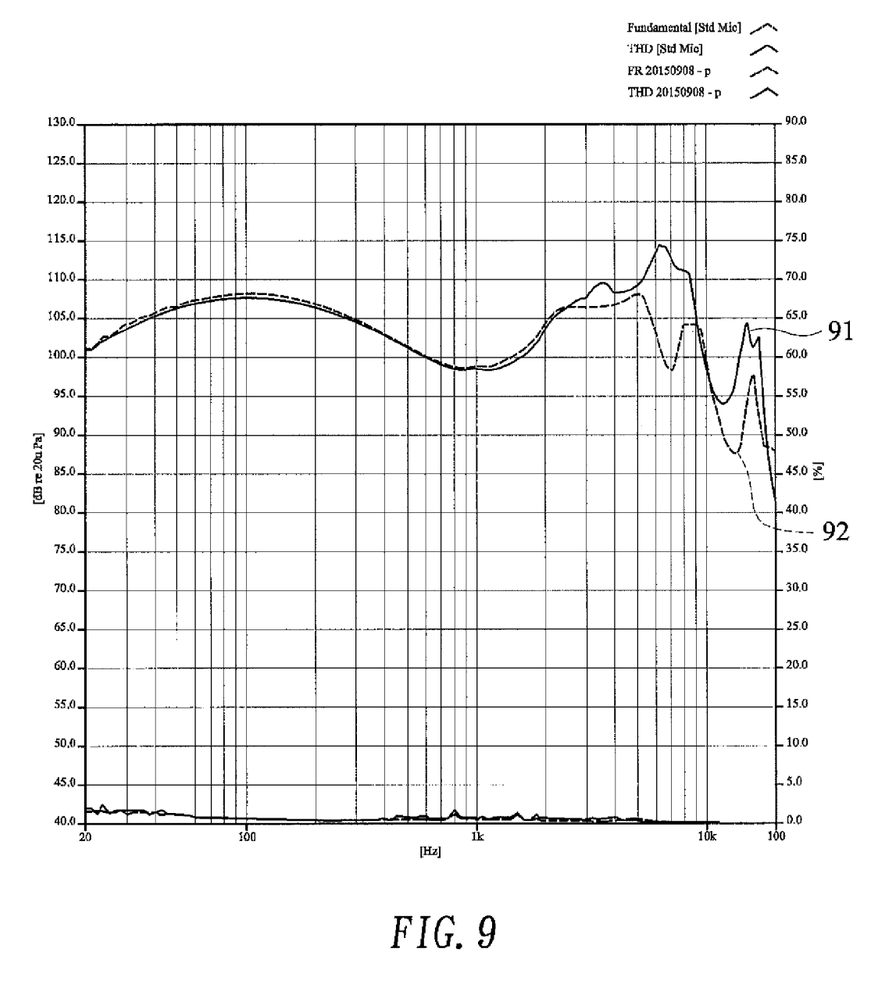
FIG. 9 is a sound frequency response curve of a waterproof earphone structure made of silicone in accordance with a preferred embodiment of the present invention and a conventional waterproof earphone cover made of mesh fabric.

With reference to FIG. 9 for the sound frequency response curves 91, 92 of a waterproof earphone structure 100 made of silicone and a conventional earphone made of waterproof mesh cloth respectively, the waterproof earphone structure 100 maintains the original sound quality without sound distortion.

The embodiments described above are intended only to demonstrate the technical concept and features of the present invention so as to enable a person skilled in the art to understand and implement the contents disclosed herein. It is understood that the disclosed embodiments are not to limit the scope of the present invention. Therefore, all equivalent changes or modifications based on the concept of the present invention should be encompassed by the appended claims.

What is claimed is:

1. A waterproof earphone structure, comprising a main body, a speaker body and a waterproof module; the main body having a rear cavity, a cavity module and a front cavity; the rear cavity being a hollow block with an end surface formed as an opening and the other end being penetrated to form a penetrating hole, and a receptacle being protruded and formed on an inner wall of the rear cavity and configured to be corresponsive to the penetrating hole, and the receptacle being communicated to the penetrating hole, and the receptacle having a diameter smaller than the diameter of the penetrating hole, a waterproof bushing being installed to a peripheral wall of the rear cavity and communicated to the interior of the rear cavity and tightly fitted with the rear cavity; the front cavity being a hollow block installed at the opening of the rear cavity; the cavity module being a circular body sheathed on an end of the front cavity and installed between the rear cavity and the front cavity; the speaker body being installed in the main body and having an audible end installed at the front cavity and configured to be corresponsive to a hollow position of the front cavity; the waterproof module being installed at the rear cavity of the main body and having a first waterproof element, and the first waterproof element having a block with a plurality of pores, and the pores being arranged, penetrated, and formed at the first waterproof element, and the pores at two opposite end surfaces of the first waterproof element being formed as apertures, and the first waterproof element being installed at the receptacle of the rear cavity and abutted at an inner wall of the receptacle, and the first waterproof element having an end surface disposed in the rear cavity and the other end surface facing outward.

2. The waterproof earphone structure according to claim 1, wherein the front cavity has a mounting portion, an output tube and an extension portion, and the mounting portion and the output tube are formed at two opposite ends of the front cavity, and the output tube is protruded and formed at the front cavity, and the mounting portion is depressed and formed at the central position of the front cavity, and the output tube has a through hole formed in an axial direction and communicated to the mounting portion, and the extension portion is axially protruded and formed at an end surface of the front cavity that forms the mounting portion; the waterproof module further includes a second waterproof element, and the second waterproof element has a structure identical to that of the first waterproof element, and the pores of the first waterproof element and the second waterproof element have a diameter smaller than 0.6 mm, and the second waterproof element is installed in a through hole of the output tube of the front cavity and coupled to an inner wall of the output tube, and the second waterproof element has an end surface configured to be corresponsive to the audible end of the speaker body; the speaker body is installed at the mounting portion of the front cavity, and the audible end of the speaker body is configured to be corresponsive to the front cavity and a hollow position of the output tube.

3. The waterproof earphone structure according to claim 2, wherein the rear cavity has a groove depressed and formed on an inner wall of the opening of the rear cavity; the extension portion of the front cavity is a plurality of plates formed at the mounting portion with an interval apart from each other, and the extension portion has a flange radially protruded and formed on an outer wall of the extension portion and opposite to the other end of the mounting portion; the opening of the rear cavity opening has a circular base depressed and formed on an end surface of the rear cavity; the cavity module has a plurality of protrusions formed on an inner wall of the cavity module and arranged with an interval apart from one another, and the extension portion of the front cavity is passed and installed to a gap formed by the protrusions; the cavity module has an end protruded to form a circular engaging portion, and the engaging portion is installed at the circular base of the rear cavity; an end of the extension portion forming the flange is accommodated in the opening of the rear cavity, and the flange of the extension portion is latched into the groove of the rear cavity.

4. The waterproof earphone structure according to claim 2, further comprising a shielding module; and the end surface of the rear cavity forming the penetrating hole being depressed to form a first mounting slot, and the first mounting slot being communicated with the penetrating hole; a second mounting slot being depressed and formed at an end surface of an output tube of the front cavity and communicated to the through hole; the shielding module having a first shielding element and a second shielding element, and the first shielding element being installed at the first mounting slot of the rear cavity and covered onto an end surface of the first waterproof element facing outward, and the second shielding element being installed in the second mounting slot of the output tube of the front cavity and covered onto the other end surface of the second waterproof element.

5. The waterproof earphone structure according to claim 4, wherein the main body further includes an earmuff; a circular slot is depressed and formed on an outer wall of the output tube of the front cavity; and the earmuff is a hollow cover, covered onto the circular slot of the output tube of the front cavity, and a hollow position of the earmuff is configured to be corresponsive to the through hole of the output tube.

6. The waterproof earphone structure according to claim 2, further comprising a shielding module; a first mounting slot being depressed and formed at an end surface of the rear cavity forming the penetrating hole and communicated to the penetrating hole; a second mounting slot being depressed and formed at an end surface of the output tube of the front cavity and communicated to the through hole; the shielding module having a first shielding element and a second shielding element, and the first shielding element and the second shielding element have a breathable mesh cloth, and the first shielding element being installed to the first mounting slot of the rear cavity and covered onto an end of the first waterproof element facing outward, and the second shielding element being installed in the second mounting slot of the front cavity output tube and covered onto the other end of the second waterproof element.

7. The waterproof earphone structure according to claim 6, wherein the main body further includes an earmuff; a circular slot is depressed and formed on an outer wall of the output tube of the front cavity; and the earmuff is a hollow cover covered onto the circular slot of the output tube of the front cavity, and a hollow position of the earmuff is configured to be corresponsive to the through hole of the output tube.

8. The waterproof earphone structure according to claim 7, wherein the rear cavity has a groove depressed and formed on an inner wall of the opening of the rear cavity; the extension portion of the front cavity is a plurality of plates formed at the mounting portion with a gap apart from one another, and the extension portion has a flange radially protruded and formed on an outer wall of the extension portion and opposite to the other end of the mounting portion; a circular base is depressed and formed at an end surface of the opening of the rear cavity; a plurality of protrusions are protruded and formed on an inner wall of the cavity module, and the extension portion of the front cavity is passed through a gap formed by the protrusions; a circular engaging portion is protruded and formed at an end of the cavity module, and the engaging portion is installed at the circular base of the rear cavity; and an end of the extension portion forming a flange is accommodated in the opening of the rear cavity, and the flange of the extension portion is latched into the groove of the rear cavity.

9. The waterproof earphone structure according to claim 1, wherein the first waterproof element is embedded into the receptacle of the rear cavity.

10. The waterproof earphone structure according to claim 1, wherein the first waterproof element is integrally formed with the receptacle of the rear cavity.

11. The waterproof earphone structure according to claim 2, wherein the second waterproof element is embedded into the output tube.

12. The waterproof earphone structure according to claim 2, wherein the second waterproof element is integrally formed with the output tube.

13. The waterproof earphone structure according to claim 1, wherein at least one pore of the first waterproof element has at least one bump.

14. The waterproof earphone structure according to claim 1, wherein at least one pore of the first waterproof element has at least one convex edge.

15. The waterproof earphone structure according to claim 1, wherein at least one pore of the first waterproof element has at least one rim.

16. The waterproof earphone structure according to claim 2, wherein at least one pore of the second waterproof element has at least one bump.

17. The waterproof earphone structure according to claim 2, wherein at least one pore of the second waterproof element has at least one convex edge.

18. The waterproof earphone structure according to claim 2, wherein at least one pore of the second waterproof element has at least one rim.

* * * * *